(12) United States Patent
Malyugin

(10) Patent No.: US 8,323,296 B2  
(45) Date of Patent: Dec. 4, 2012

(54) RING USED IN A SMALL PUPIL PHACOEMULSIFICATION PROCEDURE

(76) Inventor: Boris Malyugin, Moscow (RU)

(*) Notice: Subject to any disclaimer, the term of this patent is extended or adjusted under 35 U.S.C. 154(b) by 0 days.

(21) Appl. No.: 12/074,742

(22) Filed: Mar. 5, 2008

(65) Prior Publication Data

US 2008/0269888 A1  Oct. 30, 2008

Related U.S. Application Data

(60) Provisional application No. 60/918,405, filed on Mar. 15, 2007.

(51) Int. Cl.  
*A61F 9/00* (2006.01)

(52) U.S. Cl. ............... 606/107; 623/5.12; 606/4

(58) Field of Classification Search ............ 623/5.11, 623/5.12, 5.13, 6.4–6.42; 606/4–6, 56, 107, 606/269, 290; 600/236  
See application file for complete search history.

(56) References Cited

U.S. PATENT DOCUMENTS

| | | | |
|---|---|---|---|
| 3,975,779 A * | 8/1976 | Richards et al. ......... 623/6.55 |
| 4,321,916 A | 3/1982 | McKee | |
| 4,446,582 A * | 5/1984 | Hanna ..................... 623/6.51 |
| 4,991,567 A | 2/1991 | McCuen et al. | |
| 5,267,553 A * | 12/1993 | Graether ................. 600/236 |
| 5,318,011 A * | 6/1994 | Federman et al. ....... 600/236 |
| 5,334,217 A * | 8/1994 | Das ......................... 606/213 |
| 5,489,295 A * | 2/1996 | Piplani et al. ........... 623/1.35 |
| 6,068,643 A * | 5/2000 | Milverton ................ 606/191 |
| 6,200,336 B1 * | 3/2001 | Pavcnik et al. .......... 623/1.15 |
| 6,497,724 B1 * | 12/2002 | Stevens et al. .......... 623/1.15 |
| 6,620,098 B1 * | 9/2003 | Milverton ................ 600/236 |
| 6,814,748 B1 * | 11/2004 | Baker et al. ............. 623/1.14 |
| 7,412,993 B2 * | 8/2008 | Tzeng ..................... 140/149 |
| 7,985,180 B2 * | 7/2011 | Brown .................... 600/236 |
| 2003/0092970 A1 | 5/2003 | Lee | |

FOREIGN PATENT DOCUMENTS

| | | |
|---|---|---|
| DE | 93 20 127 U1 | 5/1994 |
| RU | 14506 U1 | 2/2000 |
| RU | 14505 U1 | 9/2000 |

OTHER PUBLICATIONS

Supplementary European Search, May 23, 2011 for PCT/US08/03472.

* cited by examiner

*Primary Examiner* — Paul Prebilic  
(74) *Attorney, Agent, or Firm* — Hamilton, Brook, Smith & Reynolds, P.C.

(57) ABSTRACT

A ring that can maintain a pupil in an extended position during an ophthalmic procedure. The ring has a plurality of loops that capture iris tissue. The ring is configured to extend the pupil when iris tissue is inserted into each loop. An ophthalmic procedure such as phacoemulsification can then be performed on the patient. The ring has a center opening that provides a wide view of the ocular chamber during the procedure.

15 Claims, 4 Drawing Sheets

FIG. 1
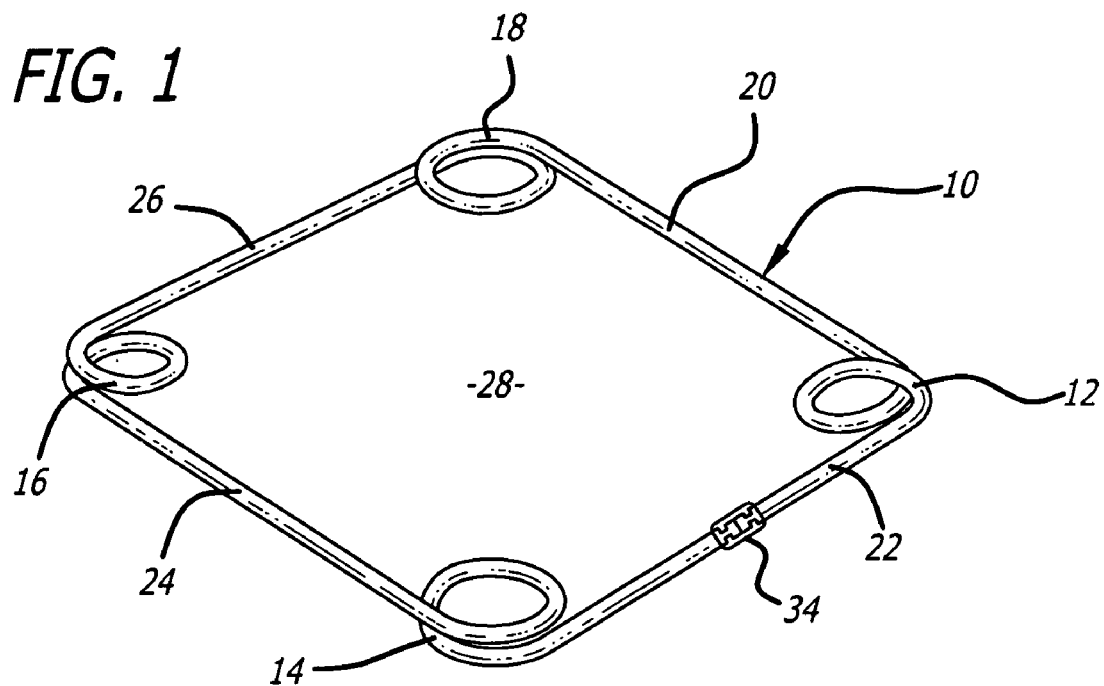
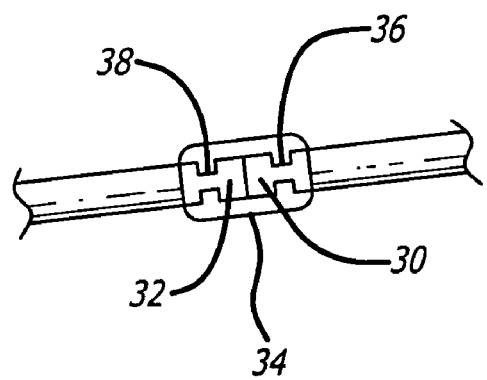
FIG. 2

RING USED IN A SMALL PUPIL PHACOEMULSIFICATION PROCEDURE

CROSS-REFERENCE TO RELATED APPLICATION

This application claims priority to Application No. 60/918,405 filed on Mar. 15, 2007.

BACKGROUND OF THE INVENTION

1. Field of the Invention

The present invention relates to a ring used in a ophthalmic surgical procedure.

2. Background Information

There are various ophthalmic procedures that require the dilation of the pupil. For example, cataracteous lenses are typically replaced in a procedure commonly referred to as phacoemulsification or phaco for short. In a phaco procedure the lens is broken up with an instrument, typically with an ultrasonically driven tool. The instrument has an aspiration port that aspirates the broken lens material from the patient's ocular-chamber.

It is desirable to extend the pupil during a phaco procedure to provide the surgeon with a wide view of the lens. One technique for extending the pupil includes pulling back the iris with a series of plastic hooks. It is has been found that using plastic hooks can cause damage to iris tissue.

BRIEF SUMMARY OF THE INVENTION

A ring used to maintain a pupil in an extended position during an ophthalmic procedure. The ring has a plurality of loops.

BRIEF DESCRIPTION OF THE DRAWINGS

FIG. 1 is an illustration of a ring of the present invention;

FIG. 2 is an illustration showing an enlarged view of the ring;

DETAILED DESCRIPTION

Figure 3:
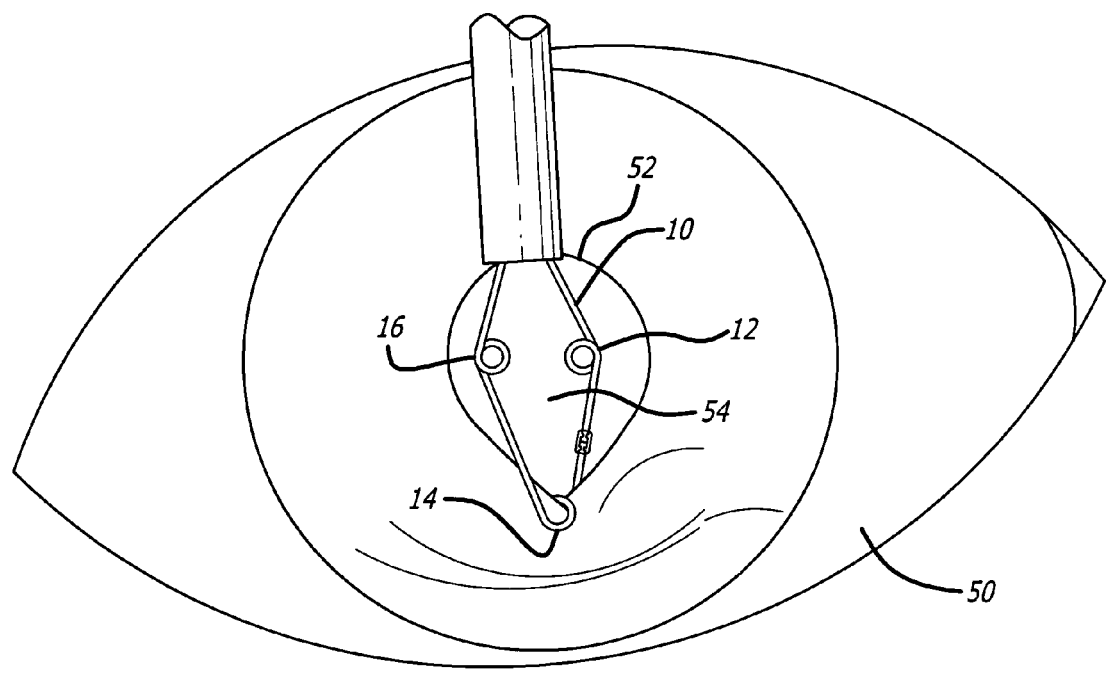
FIG. 3 is an illustration showing iris tissue being inserted into a first loop of the ring.

Described is a ring that can maintain a pupil in an extended position during an ophthalmic procedure. The ring has a plurality of loops that capture iris tissue. The ring is configured to extend the pupil when iris tissue is inserted into each loop. An ophthalmic procedure such as phacoemulsification can then be performed on the patient. The ring has a center opening that provides a wide view of the ocular chamber during the procedure.

Referring to the drawings more particularly by reference numbers, FIG. 1 shows an embodiment of a ring 10 that can be used to extend a pupil during an ophthalmic procedure. The ring 10 has a plurality of loops 12, 14, 16 and 18 located at the corners of four sides 20, 22, 24 and 26. Each loop 12, 14, 16 and 18 may be formed by one full turn. Although one full turn is shown and described, it is to be understood that each loop 12, 14, 16 and 18 may have multiple turns. The four sides 20, 22, 24 and 26 circumscribe a center opening 28.

The ring 10 preferably has a square configuration such that the sides 20, 22, 24 and 26 are of equal dimension. Although a square ring is shown and described, it is to be understood that the ring may have a rectangular configuration where all sides 20, 22, 24 and 26 are not of equal dimension. Additionally, the ring may have a non-rectangular shape. For example, the ring 10 may be shaped as a triangle that has three sides and three loops located at the ring corners. Although three and four sided rings have been described, it is to be understood that the ring may have any number of side and loops. The ring 10 is preferably constructed from a molded plastic material, although it is to be understood that other materials such as metal or plastic coated metal may be employed.

FIG. 2 shows a preferred embodiment for constructing the ring 10. One side 20 of the ring 10 has two ends 30 and 32 that are butt attached by an adhesive 34. Each end 30 and 32 may have an indent 36 and 38, respectively. The adhesive 34 can flow into the indents 36 and 38 to increase the strength of the butt attachment of the ring 10. The indents 36 and 38 create surface structure that minimizes shearing and de-lamination of the adhesive 34 from the ring 10. By way of example, the adhesive 34 may be a biocompatible material such as Class VI epoxy. The adhesive 34 can be applied with a tool (not shown) that insures a repeatable volume and dimensions of the solidified adhesive form.

Figure 4:
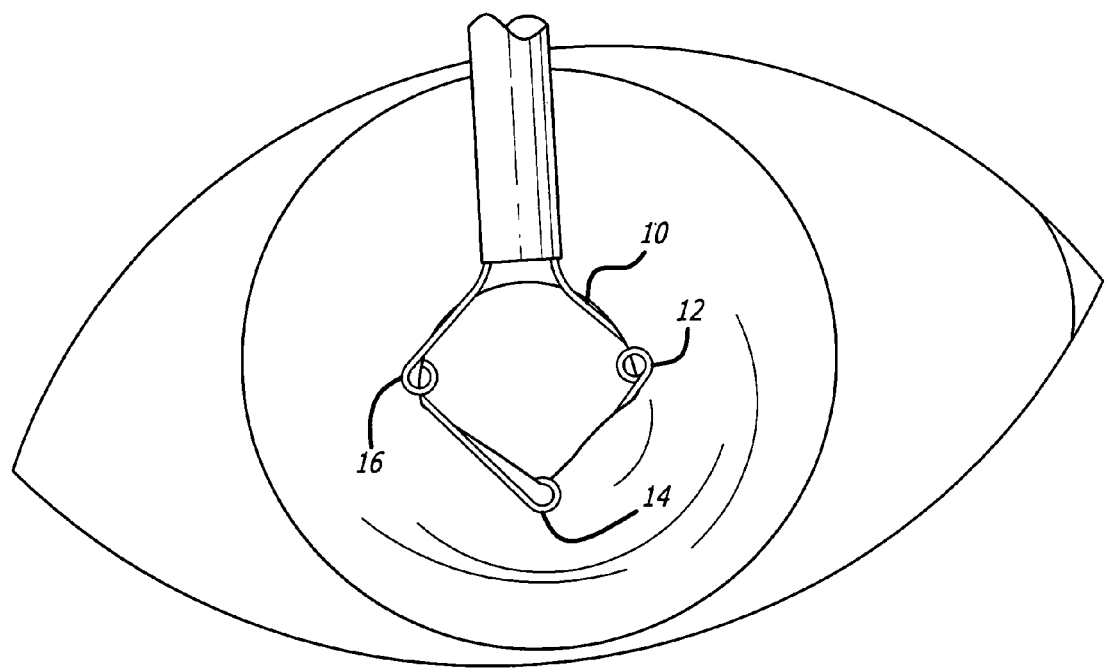
FIG. 4 is an illustration showing iris tissue being inserted into a second loop of the ring.

FIG. 3 shows the initial stages of the ring 10 being inserted into a patient's eye 50 to stretch the iris 52 and extend the pupil 54. A tool such as a forcep (not shown) can be used to pull the iris so that iris tissue is inserted into loop 14 of the ring 10. As shown in FIG. 4, the ring 10 can be manipulated so that iris tissue is inserted into loops 12 and 16.

Figure 5:
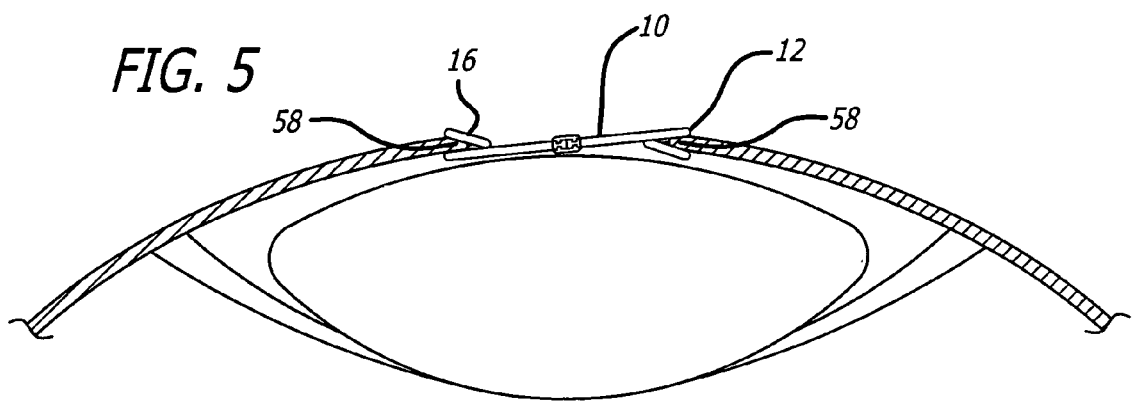
FIG. 5 is an illustration showing the iris tissue within gaps of the loops.

As shown in FIG. 1, an example of the device of the present invention is a polygonal ring formed from a single strand. As shown in FIG. 5 each loop 12, 16, etc. has a gap 58 that receives and captures iris tissue. The gap is wedge-shaped and faces the periphery of the ring 10. It is formed between a top portion of the strand and a bottom portion of the strand. The loop design provides an easy means of inserting and capturing iris tissue. The flexibility of the ring 10 allows the loops to deflect and apply a clamping force onto the iris tissue. The clamping force assists in maintaining the position of the ring relative to the eye.

Figure 6:
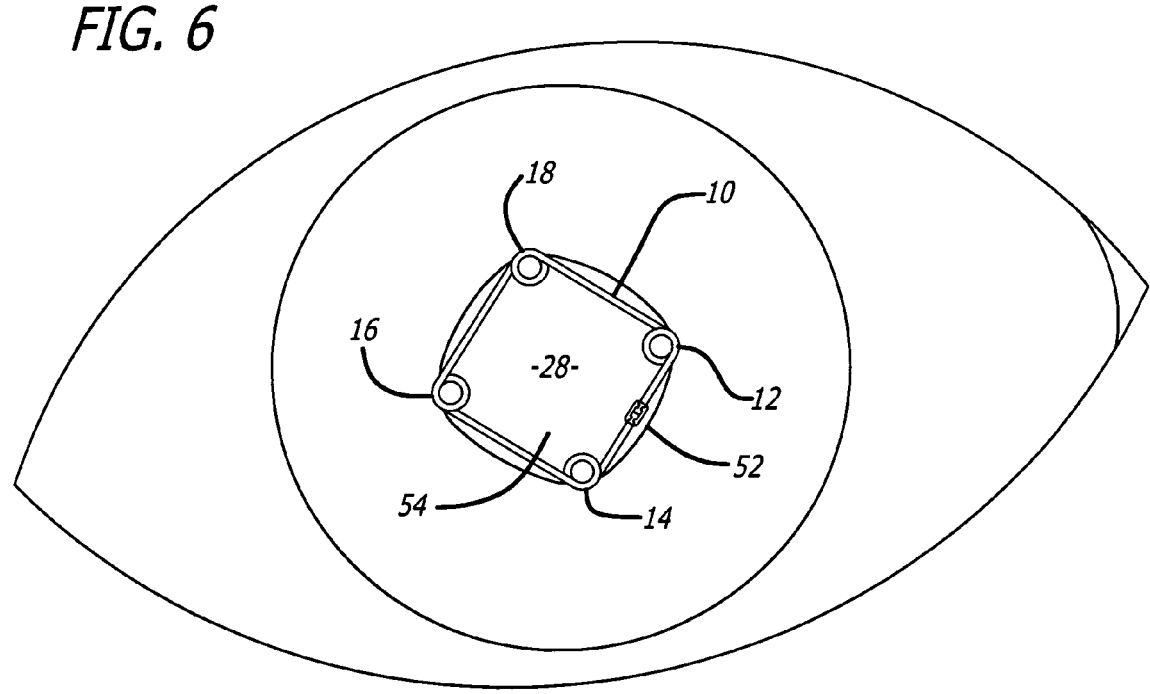
FIG. 6 is an illustration showing a pupil being maintained in an extended position by the ring.

As shown in FIG. 6 iris tissue can be inserted into the second 14 and fourth 18 loops to fully stretch the iris 52 and extend the pupil 54. An ophthalmic procedure can then be performed on the eye. For example, a phaco procedure can be performed wherein the lens is emulsified and aspirated from the eye. The ring 10 maintains the pupil 54 in the fully extended position while the center opening 28 provides a wide viewing area during the procedure. When the procedure is complete one of the sides 20, 22, 24 or 26 can be cut with an instrument and the ring 10 can be removed from the eye.

Figure 7:
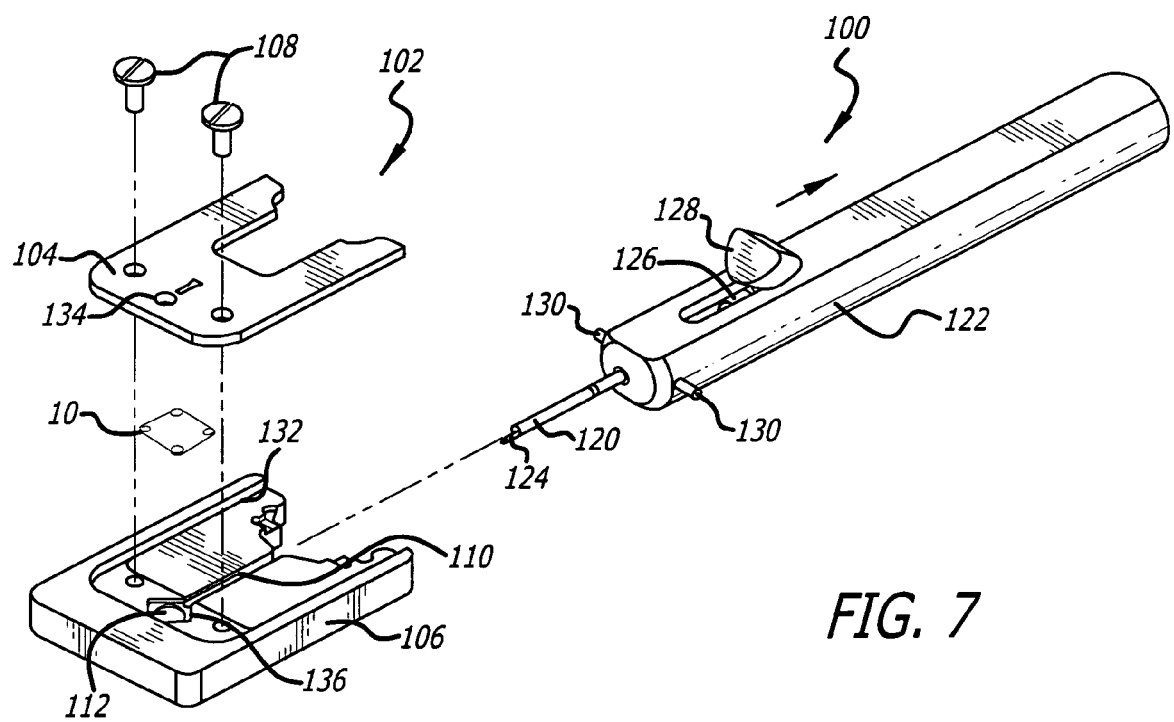
FIG. 7 is a perspective view of an injector and ring plate used to load and inject the ring.

FIG. 7 shows an embodiment of an injector 100 that can be used to inject a ring 10 into a patient's eye. The ring 10 can be loaded into the injector with the use of a ring plate 102. The ring plate 102 may include a cover 104 that is attached to a base plate 106 by fasteners 108. The base plate 106 has a channel 110 and a recess 112. The recess 112 receives the ring 10.

The injector 100 includes a cannula 120 attached to a handle 122. Within the cannula 120 is a wire hook 124. The wire hook 124 is connected to an inner slide tube 126 located within the handle 122. A button 128 is attached to the inner slide tube 126. The injector 100 may also have a pair of guide pins 130 that are attached to the handle 122 and cooperate with corresponding channel features 132 of the base plate 106 to properly align the injector 100 when the cannula 120 is inserted into the base plate channel 110.

In operation, the cannula 120 is inserted into the base plate channel 110. When fully inserted the wire hook 124 extends to approximately the center of the ring 10. The cover 104 may have an opening 134 that allows an operator to visually see the hook 124 within the ring opening. An operator then pulls the button 128 in the direction indicated by the arrow. Pulling the button 128 causes the hook 124 to grasp the ring loops and pull the ring 10 into the cannula 120. The recess 112 has tapered walls 136 to assist in the ring collapsing within the channel 112 for insertion into the cannula 120. Once loaded, the ring 10 can be injected into a patient's eye by pushing the button 128 in the opposite direction.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A ring used to maintain a pupil in a patient's eye in an extended position during an ophthalmic procedure, comprising:
   a polygonal ring formed from a single strand and located within a plane, said polygonal ring having at least three corners,
   a helical loop located at each corner of said polygonal ring, each helical loop making at least one full turn, each helical loop being disposed in the plane of the polygonal ring,
   wherein each helical loop includes a top strand portion that overlaps a bottom strand portion, the top strand portion and the bottom strand portion disposed at an angle with respect to one another, thereby forming a wedge-shaped gap facing the periphery of the polygonal ring, said wedge-shaped gap configured to capture tissue.

2. The ring of claim 1, wherein said ring is shaped as a rectangle.

3. The ring of claim 2, wherein said ring is shaped as a square.

4. The ring of claim 1, wherein each loop has more than one full turn.

5. An ophthalmic retractor, comprising:
   a rectangular frame formed from a single strand and located within a plane,
   a helical loop located at each corner of said rectangular frame, each helical loop making at least one full turn, each helical loop disposed in the plane of the rectangular frame,
   wherein each helical loop includes a top portion that overlaps a bottom portion, the top portion and the bottom portions disposed at an angle with respect to one another, thereby forming a wedge-shaped gap facing the periphery of the rectangular frame, said wedge-shaped gap configured to capture tissue.

6. The retractor of claim 5, wherein the wedge-shaped gap is configured to capture the iris of a patient's eye.

7. The retractor of claim 6, wherein the rectangular frame is a square frame.

8. The ring of claim 1, wherein the loops are positioned equidistantly along the ring.

9. A device for maintaining a patient's pupil in an extended position during an ophthalmic procedure, the device comprising:
   a polygonal ring formed from a strand, said polygonal ring including:
   a central opening,
   at least three corners, said corners being disposed equidistantly along the polygonal ring, and
   at least three side elements, each side element connecting two adjacent corners,
   each corner including a loop, each loop further including a top portion and a bottom portion, wherein:
   each side element connects the top portion and the bottom portion of two adjacent loops;
   the top portion and the bottom portion of each loop form a wedge-shaped gap facing away from the central opening.

10. The device of claim 9, wherein said polygonal ring is shaped as a rectangle.

11. The device of claim 10, wherein said polygonal ring is a square.

12. The device of claim 9, wherein said polygonal ring includes four loops.

13. The device of claim 9, wherein each loop makes more than one full turn.

14. The device of claim 9, wherein the polygonal ring is configured to adapt one or more of configurations selected from a folded configuration or an extended configuration.

15. The device of claim 9, wherein the strand includes a first end and a second end, said first and second ends being attached to each other.

* * * * *